United States Patent [19]
Bird et al.

[11] Patent Number: 5,484,906
[45] Date of Patent: Jan. 16, 1996

[54] DNA CLONE ENCODING AN ETHYLENE-FORMING ENZYME, CONSTRUCTS, PLANT CELLS AND PLANTS BASED THEREON

[75] Inventors: Colin R. Bird; John A. Ray, both of Bracknell; Wolfgang W. Schuch, Crowthorne, all of England

[73] Assignee: Zeneca Limited, London, England

[21] Appl. No.: 78,175

[22] PCT Filed: Dec. 19, 1991

[86] PCT No.: PCT/GB91/02272

§ 371 Date: Aug. 2, 1993

§ 102(e) Date: Aug. 2, 1993

[87] PCT Pub. No.: WO92/11371

PCT Pub. Date: Jul. 9, 1992

[30] Foreign Application Priority Data

Dec. 20, 1990 [GB] United Kingdom ............ 9027616

[51] Int. Cl.⁶ ............ C07H 21/04; C12N 15/29; C12N 15/82; A01H 5/00
[52] U.S. Cl. ............ 536/23.6; 536/24.5; 435/6; 435/172.3; 435/240.4; 435/320.1; 800/205; 935/64
[58] Field of Search ............ 536/23.6, 24.5; 435/320.1, 240.4, 172.3, 6; 800/205; 935/64

[56] References Cited

U.S. PATENT DOCUMENTS

| 4,943,674 | 7/1990 | Houch et al. | 800/205 |
|---|---|---|---|
| 5,365,015 | 11/1994 | Grierson et al. | 800/205 |

FOREIGN PATENT DOCUMENTS

| 9012097 | 10/1990 | WIPO. |
|---|---|---|
| 9101375 | 2/1991 | WIPO. |

OTHER PUBLICATIONS

Hamilton et al. 1990 (19 Jul.) Nature 346:284–287.
Holdsworth et al 1988 Plant Molec Biol 11:81–88.
Holdsworth et al 1987 Nucleic Acids Research 15:10600.
Deikman et al 1988 The EMBO Journal 7(11):3315–3320.
Gould et al 1989 Proc Natl Acad Sci USA 86:1934–1938.
Holdsworth et al 1987 Nucleic Acids Research 15(2):731–739.
McGarvey et al 1990 (Jul.) Plant Molec Biol 15:165–167.
Hamilton et al 1991 (Aug.) Proc Natl Acad Sci 88:7434–7437.
Balague et al 1993 Eur. J. Biochem 212:27–34.
Spanu et al 1991 (Aug.) The EMBO Journal 10(8):2007–2013.
Ververidis et al 1991 (15 Feb.) Phytochemistry 30(3):725–727.

*Primary Examiner*—Patricia R. Moody
*Attorney, Agent, or Firm*—Cushman Darby & Cushman

[57] ABSTRACT

DNA clones, e.g. M13-1, comprising at least part of a gene derived from melon that encodes ethylene-forming enzyme. Such clones may comprise DNA constructs including plant promoters capable of expressing RNA in plant cells. Such constructs may be used to inhibit production of ethylene-forming enzyme in transformed plants, and thereby to produce slower-ripening fruit, particularly melons. The clones may be obtained by PCR using specific oligo-nucleotide primers.

5 Claims, 3 Drawing Sheets

FIG. 1

SEQ ID NO: 1
SEQUENCE TYPE: Nucleotide
SEQUENCE LENGTH: 515 base pairs

STRANDEDNESS: single
TOPOLOGY: linear
MOLECULE TYPE: DNA

ORIGINAL SOURCE ORGANISM: Cantaloupe melon var. Western Shipper
IMMEDIATE EXPERIMENTAL SOURCE: Polymerase chain reaction of genomic DNA FEATURES:
from 1 to 23 bp   PCR primer
from 1 to 27 bp   exon
from 28 to 116 bp intron
from 117 to 515 bp exon
from 494 to 515 bp PCR primer PROPERTIES: M13-1 : Fragment of melon genomic DNA with homology to tomato pTOM13

```
GCATGTGAGA ATTGGGGGTT CTTTGAGGTA AATATCTCTA TAAATTCATC ATAAACTCGT    60
TACCTTAAAG CTTCTGGGTT ATTTATTTAT GAGCTGATGG TTTTTTTTGT TTGAAGTTGG   120
TGAATCATGG GATATCACAT GAGCTGATGG ACAAAGTGGA GAAGCTGACA AAGGAGCATT   180
ATAGAAAGTG TATGGAACAG AGGTTTAAAG AAATGGTAGC TTCAAAAGGG TTGGCTTCAG   240
TGGAAACTGA GATTAACGAC ACTGACTGGG AAAGCACTTT TTTTCTACGC CATCTTCCAG   300
TTTCAAACAT GTCAGAAATT GGTGATCTGG ATGAGGAATA CAAGAAGGTG ATGAAGGAAT   360
TTGCAGATGA ATGGGAGAAA TTAGCAGAGG AAGTTCTGGA TTGTGTGTGT GAGAATCTTG   420
GGCTTGAAAA AGGGTATTTG AAAAAAGTGT TTTATGGATC AAAAGGCCCA AACTTTGGGA   480
CAAAAGTTAG CAATTACCCC CCATGTCCTA AACCA                             515
```

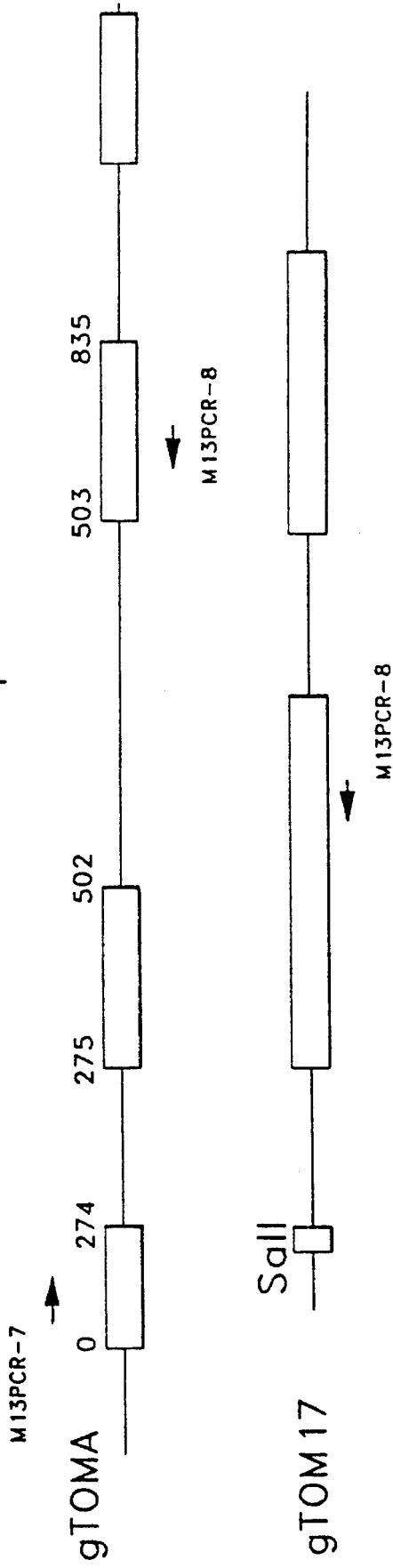
FIG. 2 ISOLATION OF MELON pTOM13 – OLIGO DESIGN

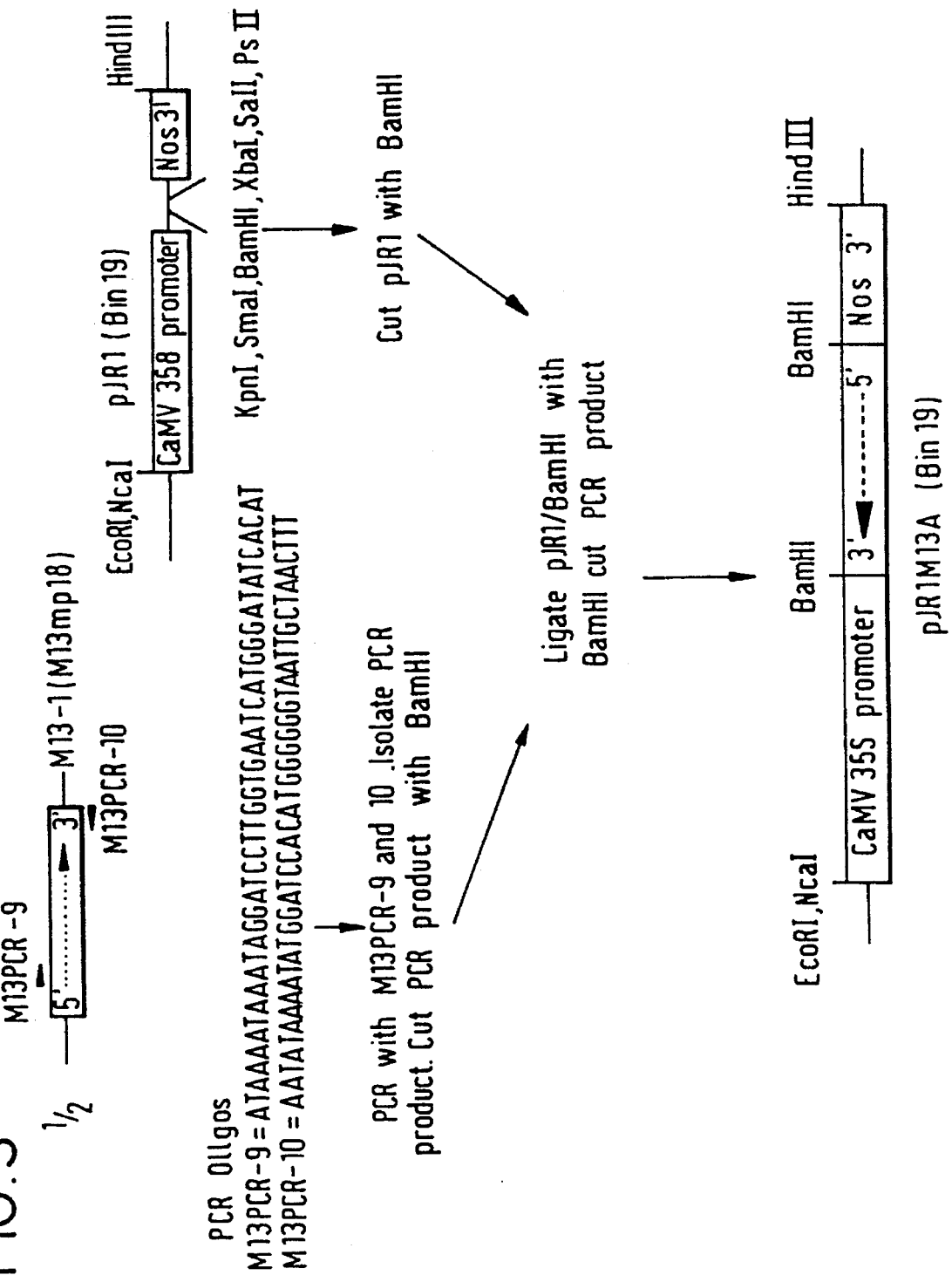
FIG. 3 Construction of pJR1M13A

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 515 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GCATGTGAGA  ATTGGGGGTT  CTTTGAGGTA  AATATCTCTA  TAAATTCATC  ATAAACTCGT    60

TACCTTAAAG  CTTCTGGGTT  ATTTATTTAT  TTCTTTGTTT  TTTTTTTTGT  TTGAAGTTGG   120

TGAATCATGG  GATATCACAT  GAGCTGATGG  ACAAAGTGGA  GAAGCTGACA  AAGGAGCATT   180

ATAGAAAGTG  TATGGAACAG  AGGTTTAAAG  AAATGGTAGC  TTCAAAAGGG  TTGGCTTCAG   240

TGGAAACTGA  GATTAACGAC  ACTGACTGGG  AAAGCACTTT  TTTTCTACGC  CATCTTCCAG   300

TTTCAAACAT  GTCAGAAATT  GGTGATCTGG  ATGAGGAATA  CAAGAAGGTG  ATGAAGGAAT   360

TTGCAGATGA  ATTGGAGAAA  TTAGCAGAGG  AAGTTCTGGA  TTTGTTGTGT  GAGAATCTTG   420

GGCTTGAAAA  AGGGTATTTG  AAAAAAGTGT  TTTATGGATC  AAAAGGCCCA  AACTTTGGGA   480

CAAAAGTTAG  CAATTACCCC  CCATGTCCTA  AACCA                               515
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asp  Ala  Cys  Glu  Asn  Trp  Gly  Phe  Phe
 1                    5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Asp  Ala  Ser  Glu  Lys  Trp  Gly  Phe  Phe
 1                    5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Tyr  Pro  Pro  Cys  Pro  Lys  Pro  Asp  Leu
 1                    5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Tyr  Pro  Pro  Cys  Pro  Gln  Pro  Glu  Leu
    1                      5

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GATGCATGTG AGAATTGGGG NTTYTT                                                      2 6

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AAATCTGGTT TAGGASATGG NGGRTA                                                      2 6

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATAAAATAAA TAGGATCCTT GGTGAATCAT GGGATATCAC AT                              4 2

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AATATAAAAT ATGGATCCAC ATGGGGGGTA ATTGCTAACT TT                              4 2

DNA CLONE ENCODING AN ETHYLENE-FORMING ENZYME, CONSTRUCTS, PLANT CELLS AND PLANTS BASED THEREON

This application relates to novel DNA constructs, plant cells containing the constructs and plants derived therefrom. In particular it involves the use of antisense or sense RNA technology to control gene expression in plants.

BACKGROUND OF THE INVENTION

Many physiological and developmental processes are controlled by ethylene in higher plants, including melon (*Cucumis melo*). These processes include fruit ripening where ethylene may be involved in both the initiation and rate of continuation of many of the changes involved in fruit ripening. However the exact role of ethylene has hitherto not been fully understood. We have now isolated novel DNA involved in the generation of ethylene in melons. In this invention, we provide such novel DNA, and methods of using it. One such use is a method for controlling the rate of production of ethylene in ripening melons. In this way the rate of many of the ethylene-related changes associated with fruit ripening on a plant can be modified according to the characteristics that are required.

As is well known, a cell manufactures protein by transcribing the DNA of the gene for that protein to produce messenger RNA (mRNA), which is then processed (eg by the removal of introns) and finally translated by ribosomes into protein. This process may be inhibited by the presence in the cell of "antisense RNA". By this term is meant an RNA sequence which is complementary to a sequence of bases in the mRNA in question: complementary in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes has been described, in for example European Patent publication no 271988 to ICI (corresponding to U.S. Ser. No. 119,614). Reduction of gene expression has led to a change in the phenotype of the plant: either at the level of gross visible phenotypic difference e.g. lack of anthocyanin production in flower petals of petunia leading to colourless instead of coloured petals (van der Krol et al, Nature, 333, 866–869, 1988); or at a more subtle biochemical level e.g. change in the amount of polygalacturonase and reduction in depolymerisation of pectins during tomato fruit ripening (Smith et al, Nature, 334, 724–726, 1988; Smith et al., Plant Molecular Biology, 13, 303–311, 1990) Thus antisense RNA has been proven to be useful in achieving downregulation of gene expression in plants.

SUMMARY OF THE INVENTION

The present invention relates to clones of a gene which expresses ethylene-forming enzyme (EFE). EFE is involved in ethylene production, and hence in the ripening of melons. Fragments of this gene have been cloned and characterised. We postulate that they will be of use in modifying the ripening characteristics of melons. The gene in question is partially encoded in the clone M13-1, which has homology (80% encoded amino acid homology) with the clone pTOM13 from tomato disclosed by Holdsworth et al (Nucleic Acids Research 15, 731, 1987). It has been shown that the gene encoded by pTOM13 is involved in ethylene synthesis in tomatoes (Hamilton et al, Nature, 346, pp284, 1990), and its translation product is now believed to be ethylene-forming enzyme (Hamilton et al., Proc. Nat. Acad>, Sci. USA, 88, p 7434, 1991).

According to the present invention we provide a DNA clone including at least part of a gene derived from melon that encodes ethylene-forming enzyme. One example of such a clone is clone M13-1. We further provide such DNA clones including DNA constructs comprising a DNA sequence homologous to to some or all of a gene derived from melon that encodes ethylene-forming enzyme, preceded by a transcriptional initiation region operative in plants, so that the construct can generate RNA in plant cells.

In a further aspect, the invention provides such DNA clones including DNA constructs, in which the homologous gene sequence is inverted with respect to the transcriptional initiation sequence so that the construct can generate in plant cells RNA antisense to mRNA for ethylene-forming enzyme. The invention also includes plant cells transformed with constructs derived from such clones; plants derived therefrom showing modified ripening characteristics; and fruit and seeds of such plants.

PREFERRED EMBODIMENTS OF THE INVENTION

The clones of the invention may be used to transform plants to regulate the production of enzymes encoded by genes homologous to M13-1. Depending on the nature of the construct, the production of the enzymes may be increased, or reduced, either throughout or at particular stages in the life of the plant. Generally, as would be expected, production of the enzyme is enhanced only by constructs which express RNA homologous to the substantially complete endogenous M13-1 mRNA. Constructs containing an incomplete DNA sequence substantially shorter than that corresponding to the complete gene generally inhibit the expression of the gene and production of the enzymes, whether they are arranged to express sense or antisense RNA.

The present invention can be applied to a variety of plants, and in particular to melons. In this way, plants can be generated which have modified expression levels of genes with homology to M13-1 and which have modified levels of ethylene production during ripening. In this way, the time of initiation and the rate of many of the ripening processes can be controlled, so as to give improved fruit quality.

Retardation of the rate of ripening will reduce the rate of deterioration of melon fruit after harvest. As a result of this fruit may be harvested when they have reached partial or full ripeness and still have the robustness to withstand handling and transport to reach the consumer in good condition. In this way high quality ripe fruit can be made available to the consumer with reduced requirement for post-harvest treatment. High quality fruit will have improved flavour and texture.

In addition high quality fruit can be produced consistently over a wide harvest period. Such fruit can be held in store for long periods and ripened to optimal quality by the supply of exogenous ethylene.

Antisense clones according to the invention preferably comprise a base sequence at least 10 bases in length for transcription into antisense RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

The preferred DNA-for use in the present invention is DNA derived from the clone M13-1. The required antisense DNA can be obtained in several ways: by cutting with restriction enzymes an appropriate sequence of such DNA; by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences. If it is desired to produce antisense DNA, the cloning being carried out that the cut DNA sequence is inverted with respect to its orientation in the strand from which it was cut.

In new vectors expressing antisense RNA, the strand that was formerly the template strand becomes the coding strand, and vice versa. The new vector will thus encode RNA in a base sequence which is complementary to the sequence of M13-1 mRNA. Thus the two RNA strands are complementary not only in their base sequence but also in their orientations (5' to 3').

As source of the DNA base sequence for transcription, it is convenient to use clones such as M13-1. The base sequence of M13-1 is set out in FIG. 1. This clone has homology to the tomato cDNA clone pTOM13 (Holdsworth et al, cited above) which encodes tomato ethylene-forming enzyme (Hamilton et al, Proc. Natl. Sci. Acad. USA, cited above). Tomato plants expressing antisense RNA to pTOM13 have reduced rates of ethylene synthesis in ripening fruit and wounded leaves.

M13-1 has been deposited on 4 Oct. 1990 with the National Collections of Industrial and Marine Bacteria, 23 St Machat Drive, Aberdeen, Scotland, under Accession No. NCIB 40324.

Clones similar to M13-1 may be obtained by using suitable oligonucleotide primers in a polymerase chain reaction (PCR) with melon genomic DNA. Suitable oligonucleotide primers may be designed according to methods similar to those described in Example 1. Such oligonucleotide primers can be used in PCR reactions with genomic DNA from other species or varieties as required. DNA fragments synthesised in these reactions may be either cloned into suitable vectors for further characterisation or cloned directly into vectors for expression in plants. Such fragments of genomic DNA may contain introns such as those found in M13-1. The introns are not transcribed into mRNA (or, if so transcribed, are subsequently cut out). When using such a gene as the source of the base sequence for transcription it is possible to use either intron or exon regions.

Alternatively, cDNA clones homologous to M13-1 may be obtained from the mRNA of ripening melons by well-known methods (kits for the purpose are available from various manufacturer, e.g., Amersham). In this way may be obtained sequences coding for the whole, or substantially the whole, of the mRNA produced by M13-1. Suitable lengths of the cDNA so obtained may be cut out for use by means of restriction enzymes. cDNA clones may differ from the fragments of genomic DNA that are obtained by polymerase chain reaction in that any introns present in the genomic fragment will not be present in the cDNA. A further way of obtaining a suitable DNA base sequence for transcription is to synthesise it ab initio from the appropriate bases, for example using FIG. 1 as a guide.

Recombinant DNA and vectors according to the present invention may be made as follows. A suitable vector containing the desired base sequence for transcription (for example M13-1) is treated with restriction enzymes to cut the sequence out. The DNA strand so obtained is cloned (if desired, in reverse orientation) into a second vector containing the desired promoter sequence (for example cauliflower mosaic virus 35S RNA promoter or a melon fruit ripening-specific promoter) and the desired terminator sequence (for example the 3' of the *Agrobacterium tumefaciens* nopaline synthase gene, the nos 3' end).

According to the invention we propose to use both constitutive promoters (such as cauliflower mosaic virus 35S RNA) and inducible or developmentally regulated promoters (such as the ripe-fruit-specific promoters) as circumstances require. Use of a constitutive promoter will tend to affect functions in all parts of the plant: while by using a tissue specific promoter, functions may be controlled more selectively. Use of such a promoter has the advantage that the production of antisense RNA is under the control of a ripening-specific promoter. Thus the antisense RNA is only produced in the organ in which its action is required.

Vectors according to the invention may be used to transform plants as desired, to make plants according to the invention. Dicotyledonous plants, such as melons, may be transformed by *Agrobacterium Ti* plasmid technology, for example as described by Bevan (1984) Nucleic Acid Research, 12, 8711–8721. Such regenerated transformed plants may be reproduced sexually, or by cell or tissue culture. Other known methods, such as particle gun technology, may be used where convenient.

The degree of production of antisense RNA in the plant cells can be controlled by selection of plants having a desired level of reduced ethylene synthesis. This can be achieved by suitable choice of promoter sequences, or by selecting the number of copies, or the site of integration, of the DNA sequences according to the invention that are introduced into the plant genome. In this way it may be possible to modify ripening or senescence to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants.

Our invention further comprises a general method of making DNA clones showing homology to genes coding for ethylene-forming enzyme which comprises submitting a plant DNA library to a polymerase chain reaction using the primers shown in FIG. 2 hereof, and recovering amplified DNA clones therefrom.

Our invention further comprises a process of isolating DNA of interest from a plant, which comprises preparing a plant DNA library, probing the cloned library with a probe comprising DNA from a clone according to the invention and recovering DNA that binds to the probe.

As well as their use in transforming plants, the clones and oligonucleotide primers disclosed herein may be used for other purposes. In particular, they may be used to identify other regions of plant DNA of interest, particularly from melons. Thus our invention includes processes for isolation and identification of DNA of interest from a plant. These processes use the clones as hybridisation probes to identify related sequences in libraries of cloned plant genomic DNA, e.g. cDNA. In addition, the oligonucleotide primers may be used in polymerase chain reactions to amplify related sequences. In this way may be recovered, from melon DNA for example, a number of other genes showing homology with M13-1. These may be partial or full length genomic or cDNA sequences encoding isozymes of melon ethylene-forming enzyme or other related oxidases. They may also include other gene elements, for example inducible promoters. It is very possible that the ethylene-forming enzyme produced in response to plant wounding is from a gene different from that which produces ethylene during fruit ripening: the clones of our invention may be used to isolate various members (isozymes) of the EFE gene family. In this way, the various physiological processes involving ethylene may be controlled by the methods described in this invention.

BRIEF DESCRIPTION OF THE DRAWINGS

The invention will now be described further with reference to the accompanying drawings, in which:

FIG. 1 shows the nucleotide sequence of M13-1 (SEQ ID NO:1);

FIG. 2 is a diagram showing the design of oligonucleotide primers for PCR reactions to amplify fragments of pTOM13-related genes from melon (pTOM13gTOMA/M13PCR-7 are SEQ ID NO:2; pE8/M13PCR-7 is SEQ ID NO:3; pTOM13-gTOMA/M13PCR-7 are SEQ ID NO:4; pE8/M13PCR-8 is SEQ ID NO:5; OLIGO/M13PCR-7 is SEQ ID NO:6; and OLIGO/M13PCR-8 is SEQ ID NO:7);

FIG. 3 is a diagram showing the construction of the clone pJR1M13A (M13PCR-9 is SEQ ID NO:8; and M13PCR-10 is SEQ ID NO:9).

EXAMPLE 1

Design of Oligonucleotides

Tomatoes contain at least three genes related to pTOM13 (GTOM17, GTOMA and GTOMB—see Holdsworth et al., Plant Mol. Biol., 11, pp 81–88, 1988). A further tomato ripening related gene sequence, E8, has been shown to have limited homology with pTOM13 (Deikman J. & Fischer R. L. EMBO J 7:3315–3320 (1988)). Two oligonucleotide primers (M13PCR7 and M13PCR8) were designed (FIG. 2), based on regions of homology between pTOM13, GTOMA and E8 (see Holdsworth et al., Nucleic Acids Research, 15, p10600, 1987), that could be used to amplify specific regions of the genes in polymerase chain reactions. These oligonucleotide primers can be used for amplification of related genes from other plant species.

EXAMPLE 2

Polymerase Chain Reactions with Melon Genomic DNA

Genomic DNA was prepared from cantaloup melon var. Western Shipper by the method described by Raeder and Broda (Lett Appl Microbiol 1, 17–20, 1985). Approximately 1 μg of genomic DNA was used in a PCR with oligonucleotides M13PCR7 and M13PCR8 (1 μg of each). The temperature of the annealing step used in the reaction was 45° for 0.2 minutes. The resulting PCR products were made blunt ended using T4 DNA polymerase and cloned into M13 mp18 cut with SmaI. Plaque lifts were made onto 'Hybond' N (Amersham) nylon membranes. The membranes were probed with $^{32}$P labelled pTOM13 at 42° C. and washed in 2×SSC, 0.1% SDS, at 42° C. Plaques which hybridised to pTOM13 were picked and DNA sequencing templates were prepared. The sequence obtained from clone M13-1 showed homology to the published sequence of pTOM13.

EXAMPLE 3

Construction of pJR1M13A

Oligonucleotides (M13PCR9, M13PCR10) were designed to amplify, by PCR, an 389 bp fragment from M13-1 which contained all of the second exon and introduced BamHI sites at both ends of the PCR product, as shown in FIG. 3. The oligonucleotides were used in a PCR with single stranded DNA from clone M13-1. The resulting PCR product was isolated from agarose, cut with BamHI and ligated with pjR1 cut with BamHI. Colony lifts were made onto Hybond N membranes and the filters probed with $^{32}$P-labelled pTOM13 at 42° C. After washing with 2×SSC, 0.1% SDS at 42° C., hybridising colonies were picked, lysed and the orientation of the melon fragment in each clone was determined by PCR with oligonucleotides M13PCR10 and NOS. A clone containing the melon fragment in the antisense orientation was designated pJRM13A.

EXAMPLE 4

Generation of Transformed Plants

Vectors are transferred to *Agrobacterium tumefaciens* LBA4404 (a micro-organism widely available to plant biotechnologists) and are used to transform tomato, melon and melon plants. Transformation of melon (De Both M. et al (1989) French patent application 8910848) tissue follows adaptations of protocols devised for other dicotyledonous plants. Transformed plants are identified by their ability to grow on media containing the antibiotic kanamycin. Plants are regenerated and grown to maturity. Ripening fruit are analysed for modifications to their ripening characteristics.

We claim:

1. A DNA clone comprising a DNA fragment that encodes ethylene-forming enzyme, said DNA fragment having the sequence of SEQ ID NO:1 found in clone M13-1.

2. A DNA clone as claimed in claim 1 in which said DNA fragment is preceded by a transcriptional initiation sequence that is operatively joined to the DNA fragment so that the clone can generate mRNA for ethylene-forming enzyme in plant cells.

3. A DNA clone comprising a DNA fragment having the sequence of SEQ ID NO:1 found in clone M13-1, in which the DNA fragment is preceded by a transcriptional initiation sequence functional in plants and is operatively joined in an antisense orientation with respect to the transcriptional initiation sequence so that the clone can generate in plant cells RNA antisense to mRNA for ethylene-forming enzyme.

4. A plant cell transformed with a DNA clone as claimed in either one of claims 2 or 3.

5. A plant comprising a plant cell as claimed in claim 4.

* * * * *